United States Patent [19]

Soane

[11] Patent Number: 5,071,531
[45] Date of Patent: Dec. 10, 1991

[54] CASTING OF GRADIENT GELS

[75] Inventor: David S. Soane, Piedmont, Calif.
[73] Assignee: Soane Technologies, Inc., Livermore, Calif.
[21] Appl. No.: 345,616
[22] Filed: May 1, 1989
[51] Int. Cl.⁵ .................. B01D 61/42; C25D 13/00
[52] U.S. Cl. ........................... 204/182.8; 204/180.1; 204/299 R; 249/117; 264/240
[58] Field of Search ............ 204/299 R, 182.8, 182.9, 204/182.7, 180.1; 249/117; 264/255, 261, 240; 425/174, 174.4, 143, 810

[56] References Cited

U.S. PATENT DOCUMENTS 4,417,967 11/1983 Ledley ..................... 204/182.8 X
4,893,529 2/1990 Muchnik et al. ............. 425/810 X Primary Examiner—John Niebling
Assistant Examiner—Caroline Koesther
Attorney, Agent, or Firm—Kilpatrick & Cody

[57] ABSTRACT

A method and apparatus are presented for the casting of gradient gels, without voids, in confined support structures such as thin slab-type configurations. Furthermore, by using a differential activation scheme for the casting, the method makes is possible to produce such gels in slabs of capillary cross-sectional dimension. According to a preferred method, a gradient slab gel is cast by filling a countable number of grooves in a first plate with a first gelling liquid. A gel casting region for a slab gel is formed by spacing the first plate apart from a second plate so as to provide a flow path between the first and second plates which has a directional component orthogonal to the grooves. A second gelling liquid is injected into the gel casting region between the plates, such that the first liquid mixes with the second liquid as the second liquid encounters each groove, thereby forming a gelling mixture with a composition gradient. The gelling mixture is then caused to gel in the gel casting region, thereby forming a gradient slab gel.

22 Claims, 3 Drawing Sheets

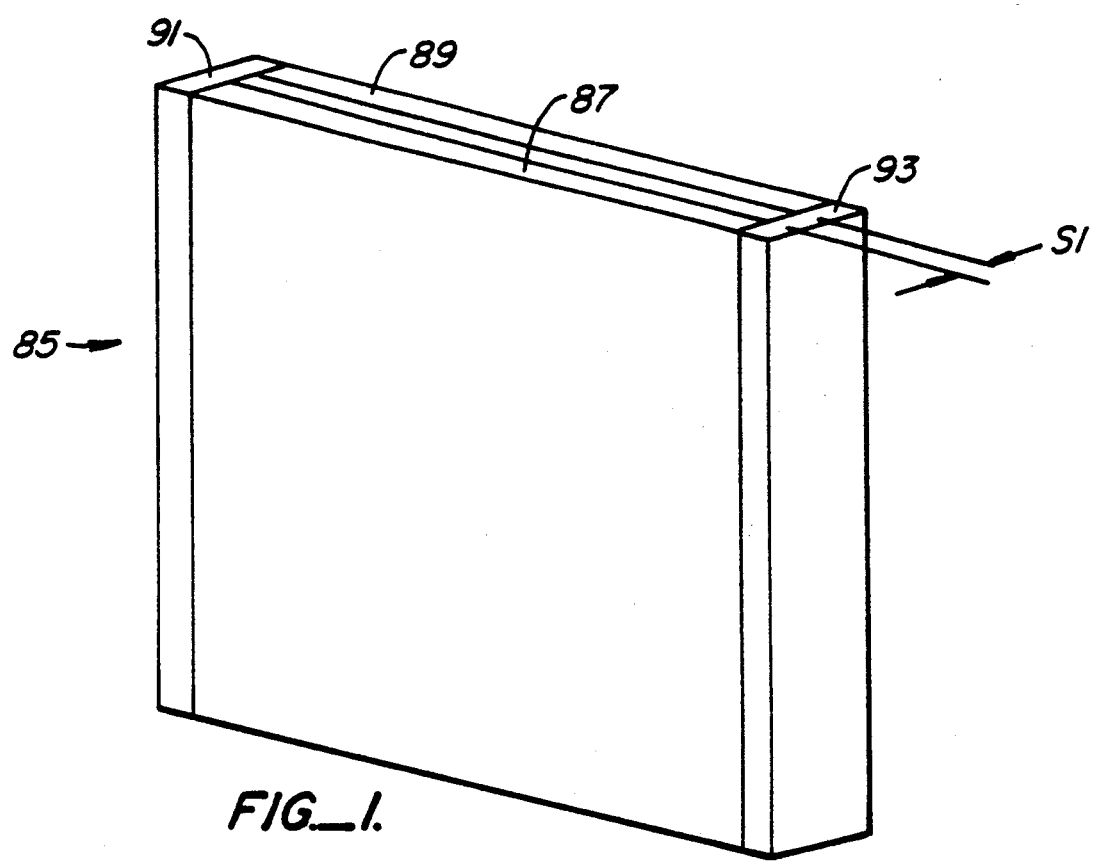
FIG._1.
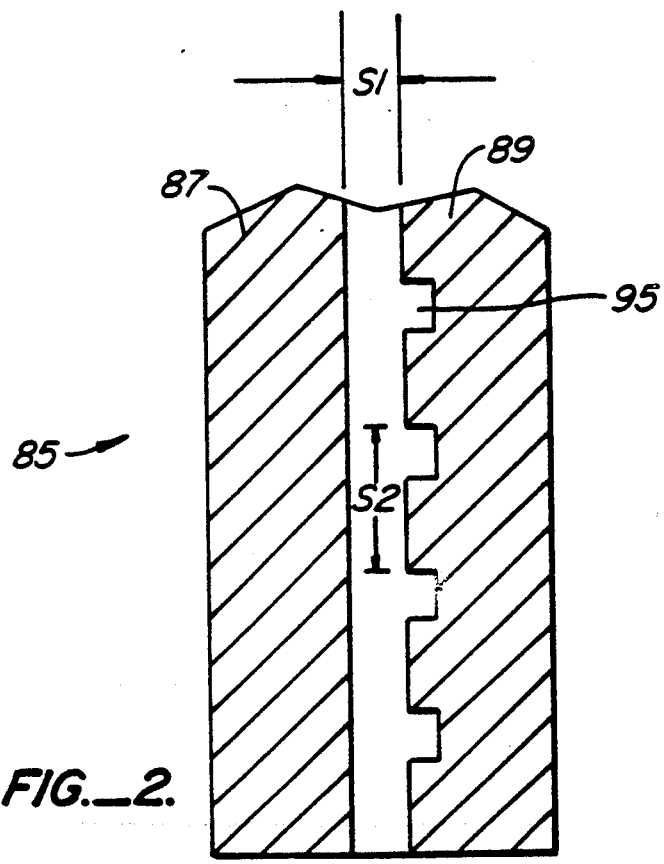
FIG._2.

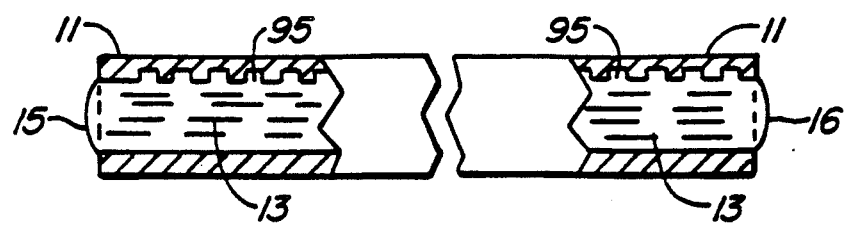
FIG._3A.
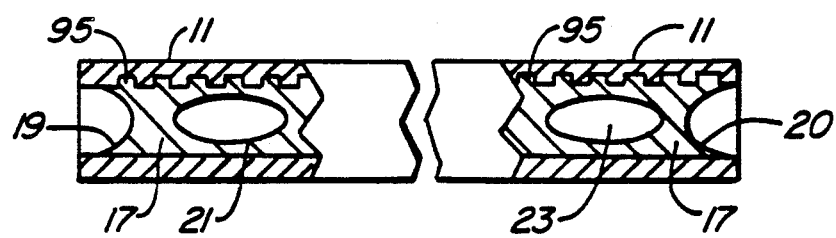
FIG._3B.
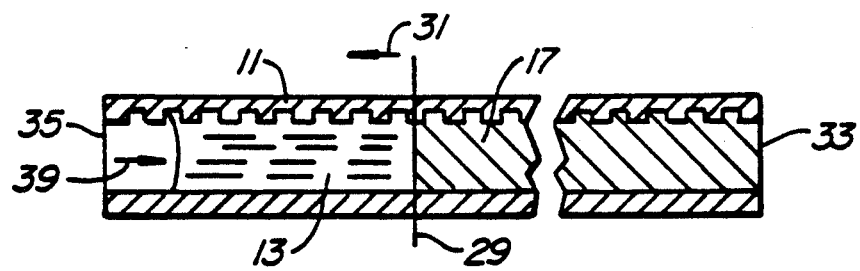
FIG._4A.
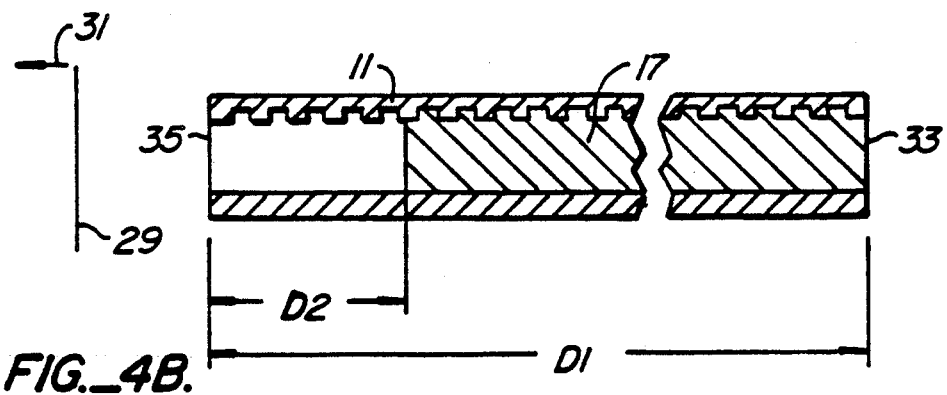
FIG._4B.

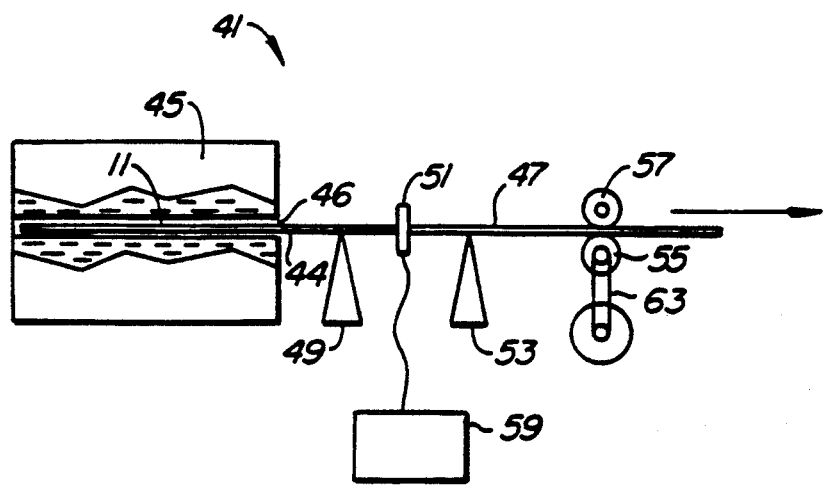
FIG._5A.
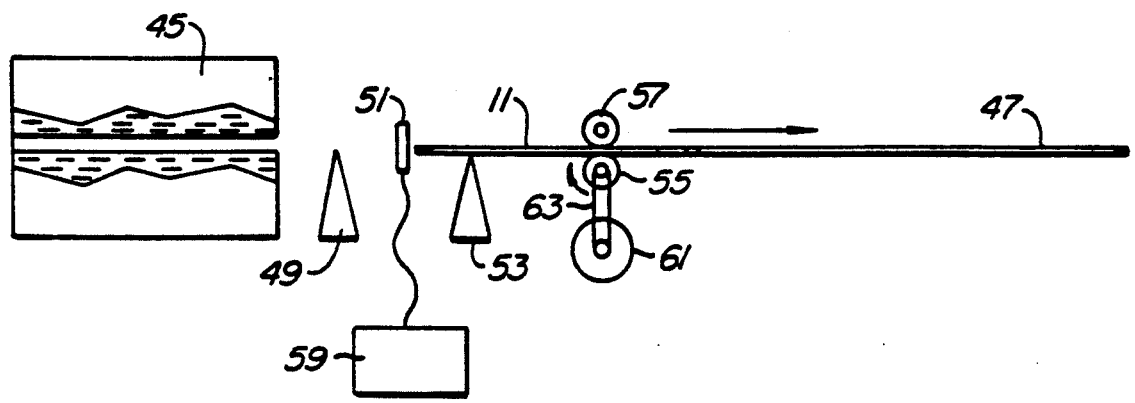
FIG._5B.
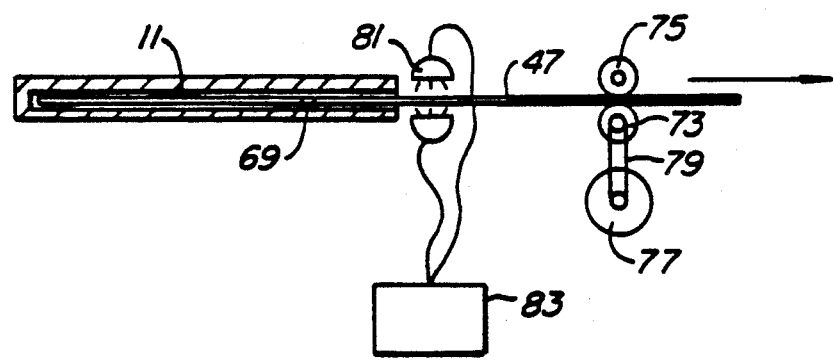
FIG._6.

CASTING OF GRADIENT GELS

FEILD OF THE INVENTION

The present invention is in the field of gel casting, and relates more particularly to apparatus and methods for casting gradient gels in narrow slabs for gel electrophoresis, gels which are particularly suited to the separation of biomolecular species.

BACKGROUND OF THE INVENTION

The separation of macromolecules from biological samples by electrophoretic techniques has been a relatively common practice for at least twenty years, and many different devices and techniques have been developed to accomplish various desirable ends. Early techniques involed imposing an electric field across a slab of gel and placing a sample of material to be analyzed on one end of the gel. Macromolecules exhibit varying mobility in a properly prepared gel depending on a number of variables, such as an electric charge, size and relative mass of the different species, and shape of the macromolecular species, which may be influenced by a strong electric field. Due to these variations, different species will move into and through a gel at differing rates, forming distinct bands as they move through the gel, thus accomplishing separation. The separate bands are sometimea called fractions, as they are each a portion of the original sample. After separation is accomplished in a gel, the electric field may be discontinued and the gel removed from any support that is used. There are techniques for rendering the fractions identifiable, such as staining and radioactive tagging, so a spectrum may be recorded. By comparing such spectra with empirical spectra produced from known mixtures and concentrations of such materials, the particular material of each fraction from an experimental sample may be identified. Techniques have also been developed for continuous elution of bands of separated fractions as they move off the end of a gel column.

Gel apparatus may take many different forms in the art, and, in the various different designs, the most common geometries for the gel region are gel slabs and gel columns. These structures are usually prepared by first mixing chemicals, including one or more reacting agents that promote curing of some of the liquid material into a gelled state. A support structure, such as a tube, or two spaced apart flat plates, is then filled with the mixture, and reactions take place to form the gel in the support structure. Typically a starting material is a monomer, an initiator, and one or more of several cross-linking agents, and surfactants. An aqueous buffer is typically included to provide an electrically conductive medium in the gel, compatible with buffers that may be used outside the gel in an electrophoresis system. Other chemicals, such as Urea as a denaturing agent, may be included as well. Gels may be of different composition as well, two common compositions being polyacrylamide and agarose, although agarose gels are, in the strict sense, not polymer gels.

In gel electrophoresis, the gel is commonly cast in an aqueous solution including an ionic buffer, and an electrical potential is applied across the gel. The electrical potential is responsible for the force causing molecules to migrate through the gel, also induces an electric current. The passage of the electric current in traditional systems, with gel slabs and columns having thickness and diameters of several millimeters and greater, has been a problem in many instances due to Joule heating. Such heating, for example, can cause distortion of the gel structure and subsequent interference with the separation process. To overcome the Joule heating effects, electrophoresis apparatus is often complicated and bulky, including elaborate elements and structures for removing heat.

The heating problem has led in the art to construction of apparatus with smaller and smaller gel structures. At the present time, the industry is headed toward the use of very thin slabs and rectangular and cylidrical capillaries filled with gel. In principle, the thin-wall and small diameter structures should prove very effective as the surface area of the supporting structures relative to the bulk of the gel is larger than in traditional structures. Although the heat per unit volume generated would be the same, the heat transfer away from the gel should be facilitated. In these thin structures, the preferred thickness of slabs would be in the range of from tens to hundreds of microns. A number of recent publications discuss the relative merits of capillaries of narrow dimensions for gel electrophoresis, for example, see A. S. Cohen and B. L. Karger, J. Chromatography, 397, 409 (1987) and S. Hjerten, et al., J. Chromatography, 403, 47 (1987).

The usefulness of a cast gel for biomolecular separation procedures depends upon a number of variables. The relative degree of crosslinking is important to the migration of macromolecules, for instance, and the homogeneity of the gel may be important. In many cases, the gel must be firmly adhered to the walls of the support structure, typically glass or plastic, so that the gel material does not migrate in the system due to electroendosmosis. Some work has been performed in this area as reported in Hjerten et al. (ibid ), which described the importance of wall treatment in suppressing adsorption of sample solutes onto the walls. Such coatings included for example, methylcellulose or linear polyacrylamide.

The gel must be continuous, too. The appearance of voids, particularly with thin slabs of capillary dimensions, can render a gel structure useless. A void can cause an anomaly in the continuity of the electrical circuit, or may seriously alter the nature of macromolecular bands as they migrate. The appearance of such voids has been a particularly vexatious problem in the preparation of such gels in systems of capillary dimensions, despite the fact that extensive fundamental research concerning the polymerization kinetics and product gel behavior has been reported in the literature. (see, for example, A. Chrambach and C. Rodbard, Separation Sciene, 7, 213 (1981; ) C. Gelfi and PIG. Righetti Electrophoresis, 2, 213 and 220 (1981); and P. G. Righetti, et al. Electrophoresis, 2, 291 (1981).)

In the casting of slab gel structures, there are applications for which it is desirable that the composition of gel vary along one direction. For example, by having a varying "pore" size, a wider range of sizes of molecules can be better separated. The resulting gel structure is called a gradient gel. At the present time, such slabs with a gradient in compstition are made using a mixing pump to premix the monomer/crosslinker/buffer solution continuously in order to vary the mixture composition being poured onto an open-face support. This is typically accomplished by preparing a liquid gel mixture with a first set of concentrations of polymerizing materials in one reservoir, then pouring from the first reservoir onto the support structure while adding materials with a second set of concentrations of polymerizing materials to the first reservoir, so that the combined materials poured onto the support structure are successively altered. The resulting liquid mixture on the support structure is then relatively quickly polymerized (gelled) so that natural diffusion doesn't obliterate the gradient to any significant degree before gellation takes place. Then a top-face is placed over the gel. This technique is adequate for slabs of large dimension, e.g. having channels of the order of a millimeter in thickness. This process is difficult to manage and control even for open structures, and is all but impossible for narrow channels, closed slabs, where the crosslinked gel is to bind with the glass surfaces.

All of these problems need to be overcome in the casting of gel structures. What is needed is an apparatus and method for preparing gel structures that is reliable, in which the degree of crosslinking can be controlled, that results in structures without voids, and by which the polymer concentration can be varied from one end of the slab to the other.

SUMMARY OF THE INVENTION

In accordance with the preferred embodiments of the present invention, a method and apparatus are presented for the casting of gradient gels, without voids, in confined support structures such as thin slab-type configurations. Furthermore, by using a differential activation scheme for the casting, the method makes it possible to produce such gels in slabs of capillary cross-sectional dimension.

According to a preferred method of the invention, a gradient slab gel is cast by filling a countable number of grooves in a first plate with a first gelling liquid. A gel casting region for a slab gel is formed by spacing the first plate apart from a second plate so as to provide a flow path between the first and second plates which has a directional component orthogonal to the grooves. A second gelling liquid is injected into the gel casting region between the plates, such that the first liquid mixes with the second liquid as the second liquid encounters each groove, thereby forming a gelling mixture with a composition gradient. The gelling mixture is then caused to gel in the gel casting region, thereby forming a gradient slab gel.

To create such gradient gels that have reduced stress and devoid of bubbles, the preferred mode of causing the gelling mixture to gel includes activating the gelling mixture sequentially from a first location to a second location in the gel casting region. This is accomplished by causing relative motion between an activating elements and the support structure such that the activating element is moved along one of the plates from a position next to the one of the plates opposite the first location to a position next to that plate that is opposite the second location. In the typical case, the activating element is an energy source such as a heater, or a source of radiation such as UV light.

BRIEF DESCRIPTION OF THE DRAWINGS

FIG. 1 shows a support structure for casting a slab gel.

FIG. 2 shows a cross-section of the structure of FIG. 1 for casting slab gels having variable composition along one direction.

FIG. 3A is a cross-section of the slab gel structure of FIG. 1 that is filled with a liquid mixture to be gelled.

FIG. 3B is cross-section of the slab gel structure of FIG. 1 after gellation of the liquid mixture.

FIG. 4A is a cross-section of the slab gel structure of FIG. 1 with gellation occuring at a moving front.

FIG. 4B is a cross-section of the slab gel structure of FIG. 4A after gellation is complete.

FIG. 5A shows an apparatus and set-up for causing gellation of liquid mixture in the slab gel structure of FIG. 1, the configuration of the set-up being before gellation is begun.

FIG. 5B shows the apparatus and set-up of FIG. 5A after gellation is complete.

FIG. 6 shows an apparatus and set-up for causing gellation using electromagnetic radiation.

DESCRIPTION OF THE PREFERRED EMBODIMENTS

Shown in FIG. 1 is a support structure 85 for a slab gel according to a preferred embodiment of the invention. The support structure 85 includes plates 87 and 89, and edge seals 91 and 93. The figure is not to scale, and the spacing S1 between the plates has been exaggerated for purposes of illustration. The spacing S1 is typically quite thin so that a very thin gel may be cast therein. Although the gel is not shown in this figure, hereinafter, the support structure 85 together with the gel therein will be called a slab gel structure and will be labeled as element 11. In the preferred mode, the spacing S1 is about 100 microns. Furthermore, in some instances, the spacing may be even smaller, say 50 microns, or even as small as 10 microns, although at such small spacing it is more difficult to keep the apparatus dimensionally stable. Other larger spacing may be also used, for example as large as 1000 microns. However, as the spacing gets larger, the differential method of gellation according to the invention which will be described subsequently is generally not as important, since at some point there is sufficient distance between the plates that the average stress in the gel due to shrinkage is not high enough to cause cavitation, one of the problems which is solved by the present invention.

FIG. 2 is a partial section through the support structure of FIG. 1, and shows plates 87 and 89 in vertical section and enlarged to show additional detail. Width S1 between the plates is shown much larger relative to the plates than is the actual case, so that the details can be made more apparent. There is a series of shallow grooves across the width of plate 89, of which groove 95 is typical. In the preferred mode, the grooves are about equally spaced, and the width and dept of the grooves can vary considerably depending upon the desired composition of the gel between the plates. In a typical case, with the spacing S1 of about 100 microns, the depth of the grooves is about 50 microns, the spacing S2 between grooves is about 1 mm, and the width of a groove is about 75 microns. These dimensions can vary, however, depending on the particular concentrations of materials used in the gel mixture, and depending on the particular application for which the gel will be used. In practice, it appears that a useful spacing between grooves varies from about 0.1 mm to about 1 mm. It should be appreciated, however, that these dimensions and the others provided above are presented for exemplary purposes and are not meant to be limiting as to the scope of the invention. It should also be appreciated that the spacing between grooves need not be equal, and, as should become apparent from subsequent discussion, that the spacing can be used as a convenient variable for adjusting the concentration of materials along the length of the gel.

In the preferred mode, the grooves run the full width of the plate, the first groove being cut at a first location near one end of plate 89 and the last groove cut at a second location on the plate, typically near the opposite end of the plate. It should also be understood, however, that in those instances where the slab gel is to be used in a multiplexing mode, so that there are a plurality of tracks traversing the length of the gel, it may not be necessary that the grooves be continuous across the width of the slab gel structure. In the preferred mode, the grooves are orthogonal to the direction of flow through the slab support structure. Although, the grooves could ostensibly not be perpendicular to the flow path, in most cases it is desired that the gel composition be uniform across the flow path in order to avoid band broadening, which implies use of the orthogonal geometry. Hence, in the typical case, the grooves have a direction at least a component of which is orthogonal to the flow path.

To prepare a graduated gel, the plates are typically first treated with a coupling agent as is common in the art. Then plate 89 is immersed in a first liquid gelling mixture, then wiped with the edge of another plate. The surface tension of the first liquid is such that the liquid is retained in the grooves. Next, the plates are assembled with the edge seals to provide support structure 85. One open end is then immersed in a second liquid gelling mixture, which is wicked up by capillary action. For plates spaced apart by 100 microns, capillary action is calculated to cause the liquid to rise by about 15 cm., sufficient for most thin slab gel structures. Other techniques may also be used for injection, particularly for longer structures, e.g. the second liquid can be injected from one end by siphoning, vacuum or other means. When the second liquid is introduced, as it passes each of the grooves in plate 89 while filling the space between the plates, it encounters and mixes with the first liquid in the grooves. This sequential mixing action, with each encounter providing another quantity of the first liquid, results in a mixture between the plates that has a gradient in the relative amounts of the ingredients of the two different liquids. Depending on the relative viscosities of the two materials and the relative speed of injection of the second liquid, mixing of the two liquids is often not complete as the second material passes a groove. Hence, the concentration gradient can have a rippled distribution along the length of the slab gel structure. As a result of diffusion, this can be evened out by waiting a period of time before the gel is cured, say a few minutes to a few hours, depending on how smooth of a concentration gradient distribution is desired.

After the mixing has occurred, the gel could be cured by standard techniques. For example, if the first and second gelling liquids are activated thermally, the slab gel structure could be heated to cure the gel, or if the gelling liquids are activated by electromagnetic or ionizing radiation, the slab gel structure could be cured by exposing it to those kinds of radiation. For a slab spacing S1 larger than about 1000 microns, such standard techniques can produce acceptable gels. However, as a practical matter such standard techniques typically lead to poor quality gels when the slab spacing S1 is small, as in the preferred mode described above.

Among the problems that are commonly encountered in the casting of gel structures, particularly in micro structures that have a high surface area to volume ratio, such as in these slab gel systems having capillary dimension separations between the plates, the appearance of voids has been of particular concern. It has been thought by many that voids that appear in the casting procedure were the result of outgassing of entrained gases in the liquid mixtures, and consequently, apparatus and procedures have been incorporated for outgassing the mixtures before and during curing to remove any such dissolved or entrained gases. Also it has been thought that gases are formed during the polymerization reactions. Such apparatus for outgassing is often expensive, incorporating vacuum pumps and vessels, and the procedures are time consuming and costly. In investigations leading to the present invention, it was found that bubble-like voids appearing in the process of gel casting were not pressure induced voids caused by gas at all, but most usually are voids caused by shrinkage of material in the gellation process. Relatively simple analytical techniques, such as measuring the weight and volume of a liquid mixture before gelling, and the weight and volume of the same mixture after gelling occurs, shows that there is significant shrinkage as a result of the polymerization that takes place, e.g. 20% or higher for a pure gel and 2% for a 10% gel. Shrinkage of the material, particularly if the material is adhered to the walls of a plate or other surface, causes large tensile stresses, which, if large enough, will cause voids to appear. The resulting voids relieve the tension in the gelled material, but the resulting gel is in many cases completely inoperable.

To illustrate these principles more carefully, shown in FIG. 3A is a side view, partially sectioned, of a slab gel structure 11 which has been filled with a liquid mixture 13 of materials having a concentration gradient as described before, which includes a gelling agent that will cause a primary component of the mixture to gel. Initially, the liquid fills the volume, with a small miniscus 15 and 16 at each end of the slab. The volume of the liquid is substantially the volume between the plates (ignoring the miniscus).

FIG. 3B shows the same slab gel structure at a later time after the liquid mixture has gelled. Gel 17 is shown then with the crosshatching of a solid material (although a gel is a considerably flexible substance). Shrinkage takes place in the gelling process, so gel 17 will occupy less volume than the original liquid, unless sufficiently constrained from so doing. There is, indeed, one such constraint. The gel has adhered to the walls of the support structure.

In this example, all of the material was gelled at substantially the same time, and the adhesion to the wall occurred at the time of gelling. As the material gelled, and consequently shrank, the material at the wall could not move relative to the wall, and that material formed flexible bonds with adjacent material. The material at the wall is therefore relatively more highly stressed than the material further from the wall, and the material near the center, having the most freedom of movement, is the least stressed. Part of the stress relief for the material near the center is the result of the fact that there are no end restraints, so the gelled material at the ends of the slab will take the inverted form shown approximately by end profiles 19 and 20.

In a very short slab, and in slabs of relatively large cross-section, the end movement may be the only form of stress relief in the process. In slabs of capillary dimensions, however, the length to cross-section dimension ratio is very high, and the end movement can only compensate for a very small amount of the total volume shrinkage that would be required to relieve the stress. If the percentage of volume shrinkage in an unrestrained system were 5%, for example, the end movement would have to be 5% of the total volume to produce an unstressed gel. In the typical case, however, the end movement in systems of capillary dimension is much less than that required to accommodate the shrinkage volume, so either the resulting gel is highly stressed, or another stress relief mechanism appears.

In general, the result is that the stress in the gel overcomes the cohesion between molecules of material, and voids appear, voids which look very much as bubbles would look if gas were to evolve in the material as gelling takes place. Voids 21 and 23 shown in FIG. 3B illustrate the results of this tearing effect. The voids typically appear as gelling proceeds, rather than at a later time, because the gel gains in tensile strength as polymerization proceeds, and a more highly crosslinked system, having a higher tensile strength, can support a higher tensile stress without tearing to form voids. It is true, too, that the formation of voids in this fashion does not entirely relieve the stress, as the voids only form if the stress becomes larger than the tensile strength of the material at the time of formation of the void.

In the present invention these stress related voids are eliminated by causing liquid systems between the plates to gel in a differential fashion along a moving front, so that material ahead of the moving gel zone remains liquid, and material that the front has passed is gelled. The still-liquid material ahead of the moving gel zone may then flow to that zone, at a rate that equals the rate of shrinkage, and a void-free, reduced stress gel is produced.

These principles of differential gellation are illustrated in more detail with reference to FIG. 4A, which shows a cross-section of a slab gel structure 11 similar to that shown in FIG. 3A. The slab structure of FIG. 4A was initially filled with the liquid mixture 13 as in FIG. 3A. The structure is shown as broken to indicate that the length is much greater than the cross-section. Again, a typical length for a slab structure for a gel electrophoresis apparatus is 15 cm., and a typical plate separation is 100 microns.

In the system represented by FIG. 4A, the liquid mixture does not gel all at substantially the same time. Rather, gelling occurs at a moving front, represented by plane 29, moving in the direction of arrow 31. The gelling front starts at one location in the liquid filled structure, in this instance end 33, and proceeds at a predetermined velocity to another location in the structure, in this instance the other end 35. As the gelling front passes, the liquid material gels, and material 17 "behind" the gelling front is gelled material. Adhesion to the inside wall of the capillary occurs at substantially the same time that gelling occurs.

The fact that gelling takes place with shrinkage dictates that liquid material 13 "ahead" of the moving front must flow toward the front, in the direction of arrow 39, to make up for the volume loss. The fact that the material ahead of the front remains liquid allows the flow to take place, with the result that the gelled material is substantially unstressed, and there is no tension produced to cause the bubble-like voids that are evident when the liquid material gels all at the same time.

FIG. 4B represents the condition of the gel of FIG. 4A after the gelling front has passed the full length of the slab. All of the liquid mixture has been gelled, and the space unfilled at the end of the slab where gelling last took place, represented by length D2, represents the volume contraction due to the gelling process. The ratio of D2 to the length of the slab D1, which was originally filled with the liquid mixture, will be substantially the same as the fractional contraction in the gelling process. That is, if a mixture is provided that contracts 3% in gellation, then D2 will be substantially 3% of D1, if one does not keep the end of the slab in contact with a reservoir of gelling mixture during the zone gellation process.

One way that gelling may be caused to occur at a moving front is by using a liquid mixture in which the rate of gellation is affected by absorption of energy, for example activation may be a function of temperature. In that case, the space between the two plates is filled with the gelling mixture as previously described, and the support structure filled with liquid mixture is kept at a reduced temperature, such as by immersion in an ice bath, until processing commences. The support structure is then drawn through a heated zone which heats the region next to the plates so that gellation takes place at a moving front as will be described subsequently with reference to FIGS. 5A and 5B. In practice the heated zone is typically about 2.5 cm to 5 cm in length since that is a convenient size for a resistance heater, and extends all the way across the width of the gel structure. It should be understood, however, that other lengths could also be used for the heated zone, either longer or shorter. All that is required is that the gellation zone not be so long that shrinkage cannot be compensated for as the zone is moved along the length of the slab.

FIG. 5A depicts an apparatus 41 as a preferred embodiment of the invention in which heat is used to induce gelling of a liquid mixture at a moving front. After treatment of the support structure 85 with wall coupling agents, a portion of the support structure is filled with two liquid mixtures as previously described in which gelling rate is a function of temperature.

An example of a mixture that can be used in the apparatus with the method described is as follows:

FIRST EXEMPLARY COMBINATION

First Liquid Mixture (i.e. Mixture in Grooves)

(1) Monomer: Acrylamide (20% w/v i.e. 20 gms/100 ml)
(2) Comonomer/Crosslinker: N,N'-methylenebisacrylamide (Bis, 3% w/total solid weight)
(3) Initiator: Ammonium persulfate (0.05% w/v)
(4) Coinitiator/Accelerator: N,N,N',N'-tetramethylethylene-diamine (TEMED, 0.06% v/v, i.e. 0.0006 ml/ml)
(5) Surfactant: Sodium dodecylsulfate (SDS, 0.1% w/v)
(6) Buffer: Tris/Phosphate (0.1M)
(7) Modifier: Urea (7M).

Second Liquid Mixture (1) Monomer: Acrylamide (5% w/v)
(2) Comonomer/Crosslinker: N,N'-methylenebisacrylamide (Bis, 3% w/total solid weight)
(3) Initiator: Ammonium persulfate (0.05% w/v)

(4) Coinitiator/Accelerator: N,N,N',N'-tetramethylethylene-diamine (TEMED, 0.06% v/v, i.e. 0.0006 ml/ml)
(5) Surfactant: Sodium dodecylsulfate (SDS, 0.1% w/v)
(6) Buffer: Tris/Phosphate (0.1M)
(7) Modifier: Urea (7M).

For this exemplary mixture, a 100 micron plate separation can be used, with a heated zone temperature of 43 Degrees C, a pulling rate of 0.8 cm/min. and a 5 cm heated zone length.

Those skilled in the art will appreciate that the concept of the invention is not restricted to the particular compounds described above to form the pre-gel mixture. Generally any monomer can be used which shrinks on polymerization. Hence, as a minimum set, all that is needed is a monomer and an activator to activate the monomer to cause chain lengthening, either by step process or addition. In this example, the activator is the initiator which breaks the double bonds of the monomer, a process that characterizes those monomers that can be polymerized by means of free-radical initiation. In this embodiment, the free-radical initiation is caused by a thermal decomposition initiator. For separation of biomolecules using gel electrophoresis, aqueous soluble vinyl monomers are particularly useful, other examples including acrylic acid, methacrylic acid, vinyl alcohol, vinyl acetate, methacrylamide, 2-oxazolines, and pyrrolidone derivatives such as vinyl and methyl pyrrolidone. For the acrylamide monomer of the preferred embodiment and these aqueous soluble monomers, a typical concentration is in the range of 3 to 20% w/v. For other monomers such as latex, a typical concentration of monomer can be as high as 50% w/v. (In the preferred mode example above the two concentrations of monomer at 5% and 20% w/v were chosen to give an appropriate range of gel density from one end of the slab to the other for separation of biomolecules). Other solvents may also be used for example methanol and acetonitrile. Similarly, some non-aqueous soluble monomers would include styrene, methyl methacrylate, and silanes.

In general, the basic structure of the gel is determined by the monomer. Hence, in this application, as in others which use polymer gels, a comonomer or crosslinker is typically used to change the basic structure of the gel, depending on the nature of the molecules to be separated. For polyacrylamide gels, other well-known crosslinking agents are also effective, such as N,N'-bisacrylylcystamine (BAC), N,N'-diallyltartardiamine (DATD), N,N'-(1,2-dihydroxyethylene) bisacrylamide (DHEBA), ethylene diacrylate (EDA), and others. For all of these crosslinkers, a typical range of concentrations is from 2 to 5% weight/total solid weight. Those skilled in the art will understand that other concentrations may be used depending on the desired structure and the nature of the separation to be performed. Furthermore, the gradient may be related to crosslinker concentration rather than monomer concentration, since that would provide a varying pore size from one end of the slab to the other. Also, both the monomer and crosslinker concentrations could be varied from one end of the slab to the other.

An example of a mixture which relies on variation in crosslinker concentration is a follows:

SECOND EXEMPLARY COMBINATION

First Liquid Mixture (i.e. Mixture in Grooves)

(1) Monomer: Acrylamide (15% w/v)
(2) Comonomer/Crosslinker: N,N'-methylenebisacrylamide (Bis, 2% w/total solid weight)
(3) Initiator: Ammonium persulfate (0.05% w/v)
(4) Coinitiator/Accelerator: N,N,N',N'-tetramethylethylene-diamine (TEMED, 0.06% v/v, i.e. 0.0006 ml/ml).

Second Liquid Mixture (1) Monomer: Acrylamide (15% w/v)
(2) Comonomer/Crosslinker: N,N'-methylenebisacrylamide (Bis, 5% w/total solid weight)
(3) Initiator: Ammonium persulfate (0.05% w/v)
(4) Coinitiator/Accelerator: N,N,N',N'-tetramethylethylene-diamine (TEMED, 0.06% v/v, i.e. 0.0006 ml/ml).

Other initiators may also be used, provided they are appropriate for the monomer/crosslinker combination used. For the above combinations, for example, potassium persulfate may be substituted for ammonium persulfate as an initiator. In general, however, the classes of compounds that are useful as thermal decomposition initiators for general polymerization reactions are somewhat limited and other classes that are typically used are those with O—O, S—S, or N—O bonds, since these classes of compounds exhibit bond dissociation energies in the range of 100-170 kJ/mole. Compounds with higher or lower bond dissociation energies will typically dissociate too slowly or too rapidly. A notable exception to this general rule are some azo compounds, such as 2,2'-Azobisisobutyronitrile (AIBN), which has a dissociation energy of the N=N bond of about 290 kJ/mole, but the driving force for homolysis there is the formation of the highly stable nitrogen molecule. It is expected that these compounds would behave similarly when used for polymer gel formation for separation purposes. For the more general polymer systems where thermally initiated polymerization is used, the peroxides have typically been the initiator of choice (e.g. acyl peroxides such as acetyl and benzoyl peroxides, alkyl peroxides such as cumyl and t-butyl peroxides, hydroperoxides such a t-butyl and cumyl hydro- peroxides, and peresters such as t-butyl perbenzoate).

Similarly, other accelerators may be used as catalysts for the crosslinking, particularly those that will cause the crosslinking reaction to become a stronger function of temperature. The use of crosslinkers tends to make the gel much more stable during use as well as contributing to the establishment of an effective pore size for the gel. There is also a broad range of soap-like molecules that will serve well as surfactants, such as Triton-x, Tween-x, and Brij-x. These surface modifiers are used to change the nature of the interaction of the biomolecules with water, with each other, with their environment, since these molecules are often hydrophobic and tend to stick together in aqueous solutions. The surfactants help separate the solute into individual molecules which can then migrate individually down the gel. Similarly, other appropriate buffers may be used for pH stabilization, or they may be used for control of ionic strength, since some molecules tend to bind to particular ions. Some examples of other buffers include borates, phosphates, citrates, carbonates, etc.

Various modifiers may also be used which generally are dependent on the type of molecule being analyzed, and on how the interaction of the solute with the other compounds in the gel matrix is to be altered. In the example given, the purpose of the Urea is to weaken intramolecular hydrogen bonding, which helps to ensure denaturation of any protein solutes injected into the slab gel structure. As a general rule, if it is not anticipated that biomolecules are to be separated, Urea is unnecessary, and even there separations can often be effected without it. Another useful modifier for biomolecular separations is guanadine, typically about 5M, which is sometimes used in combination with Urea. Those skilled in the art will appreciate that there are many other useful modifiers which can be used to control or change the nature of the separation process. For example, other useful modifiers include alcohol, and acetonitrile.

Although not required, the use of a wall coupling agent has been found to significantly enhance the stability of the gels produced, since the gels are then held firmly in place by the wall. Use of such wall couplings is a common practice in the art. An additional benefit of the present invention, however, is the simplicity of the preferred wall coupling procedure used. In particular, prior to filling the support structure with the mixtures of materials above which will form the gel, straight (pure) or diluted 3-methacryloxy-propyl- trimethoxysilane (MAPTMS) (in acetone solution) is used to coat the walls of the support structure. The support structure is then air dried and heated in an oven for three hours at about 130 degrees Centigrade to effect MAPTMS binding to the wall surfaces. The MAPTMS promotes strong wall adhesion and a dense, highly cross-linked gel adjacent to the wall. Although not as simple, other wall coupling agents and procedures may also be used. For example, another approach is to covalently bond aminopropyltrimethoxysilane or aminopropyltriethoxysilane to the wall. N-acryloxysuccimide is then used to cause substitution addition. This is then followed by treatment with diethylacrylamide to cause crosslinking of the materials on the wall. In all of the procedures above, the goal is to leave a wall surface covered with double bonds directly linked to the wall by chemical bonds. These double bonds can then react with acrylamide monomers and crosslinkers in the differential gellation process. In the preferred mode, the liquid mixture of the materials to be gelled in the support structure is kept at ice bath temperature (0 degrees Centigrade) during preparation (not shown) and during filling of the grooves and injection of mixture into support structure 85 (also not shown). Once the support structure is filled, it is placed in a cold chamber 45 through an opening 46 in the chamber.

A leader 47 is attached to the support structure to serve as an attachment for pulling the support structure out of the cold chamber once the process is initiated. The leader may be another length of unfilled support structure or a solid slab of substantially the same outside cross-section as the outside cross-section of the support structure 85. In the illustrated embodiment, the attachment point is point 44 between the leader and the support structure. Alternatively, a longer support structure may be used without a leader.

In the preferred embodiment, leader 47 passes over a support slide 49, through an activating system 51, over a second support slide 53, and into a set of rollers comprising a propulsion roller 55 and an idler roller 57. The propulsion roller is driven by an electric motor 61 through a belt 63. In the preferred mode, the motor has a speed control (not shown).

In the preferred embodiment, the activating system 51 is a heat ring which has a resistance heater, and an electrical controller 59 is connected to the heat ring. Other activating systems could also be used for heat-activated gellation, for example, a thermostatically controlled fluid, heated by a resistance heater is also convenient, or a laser could also be used. Also, for embodiments which do not use heat-activated gellation, the activating system 51 could be an optical system or a laser if the gellation is photoactivated, or even a beam of ionizing radiation if the gellation is activated by such radiation.

Once all the preparatory steps are made, the heat ring is brought up to temperature, and the propulsion drive is started. The liquid-filled support structure is drawn out of the cold chamber and through the heat zone. The liquid material in support structure 85 is gelled along a moving front from a first location where the activation is initiated to a second location where activation is discontinued, the first location typically being at one end of the support structure and the second location typically being at the other end of the support structure, as described above with reference to FIGS. 4A and FIG. 4B. During this process, the still-liquid material in the support structure flows toward the reaction (gelling) plane, making up for the volume shrinkage due to gellation. FIG. 5B shows the support structure drawn fully through the heat ring, and the gelling process in the support structure is complete.

As indicated earlier, the temperature of the heat ring is controlled, the temperature used being determined empirically, and generally depends on the composition of the liquid material, the distance of the ring from the support structure, the material, the separation between the plates, and wall thickness of the support structure, and the rate at which the support structure is drawn through the heated zone. In the preferred embodiment described, a temperature of about 43 degrees C. is appropriate. In other situations temperature as low as 30 degrees have been successful, and the preferred range of temperatures appears to be about 25 to 50 degrees C.

The rate at which the support structure may be drawn is controlled as well. Since the support structures used are of small cross-section, typically 10 to 1000 microns, they present a significant restriction to flow, and if the pulling speed is too high, the liquid flow will not be able to compensate for the shrinkage. The volumetric flow rate due to shrinkage is the product of the percentage actual shrinkage, the cross-sectional area of the support structure, and the pulling velocity, and is relatively easily calculated. The ability of the liquid to flow through the support structure to the moving front at a rate high enough to replace the shrinkage volume is related to the pressure differential from the open end to the gelling front. The pressure differential may be calculated by well known fluid flow equations. The result of those calculations indicates that as the cross-section becomes small, as for capillary dimensions, it is important to keep the viscosity of the flowing material low enough so that the mixture can flow sufficiently well to replace the volume lost due to shrinkage during gellation. Operationally, for the particular mixture chosen in the above example, this means that the temperature of the mixture in the unreacted portion of the support structure should be maintained well below the reaction temperature for gellation, before it is introduced into the heated reaction zone. In practical terms, this is accomplished by the ice bath for the preferred mixture described. However, for other combinations of materials and reaction temperatures, such temperatures may be better maintained by temperature controlled refrigeration systems, or may not need to be controlled other than by the ambient atmosphere if the reaction temperature is high enough and the reaction zone heater is well enough confined. Also, it is apparent that the pressure differential may be increased by pressurizing the fluid in the cold end of the support-structure.

In the preferred embodiment with the mixture described and the cold zone maintained at 0 degrees C. (ice), with a glass support structure of cross-section 0.005 cm, the pulling speed can be maintained at about 1 cm. per minute, while relying on atmospheric pressure as one limit of the pressure differential across the liquid portion of the mixture.

As indicated earlier, the use of a heat-sensitive mixture and the application of heat at a narrow region while providing relative movement between the support structure and the heat zone is just one way of creating a moving gelling front. In an alternative preferred embodiment, a liquid mixture is prepared having a gelling rate that is a strong function of exposure to electromagnetic radiation. In this embodiment, the polymerization is photoinitiated. Generally photoinitiation occurs when light absorption results in the production of radicals, typically by one of two pathways: a) one or more compounds in the system undergo excitation by energy absorption, i.e. electronic transition, and subsequent decomposition into radicals, and/or b) one or more compounds undergo excitation and the excited species interacts with a second compound (by either energy transfer or redox reation) to form radicals derived from the latter and/or former compounds(s). To accommodate this photoinitiated process, the mixture is similar to the mixture described above for thermally initiated polymerization, except a photoinitiator, such as riboflavin which is active in the ultraviolet portion of the spectrum, is used instead of initiators and accelerators that are temperature sensitive. Other aqueous photoinitiators that may be used are also well known in the art, and include azo-dicarbonamide, 1,1'-azobis (N,N-dimethyl- formamide), and sodium salts of 4,4'-azobis (4-cyanovaleric acid).

As a specific example of a mixture which can be used for a photoinitiated process, the set of ingredients would be the same as for the examples of thermally initiated mixtures above and equivalents thereof as discussed, except for the substitution of riboflavin for the initiator. In the preferred mode, the riboflavin is used at concentration of 0.005 mg/ml, and can generally be varied from 0.0005 mg/ml to 0.04 mg/ml, or even higher, and similarly for the other photoinitiators described above.

FIG. 6 shows an apparatus, similar to the apparatus for heat initiated reaction, for use with a photosensitive mixture. A support structure 85 is filled with a liquid mixture similar to the mixture described for a heat initiated reaction, except the initiator is photosensitive. Preparation is done in the absence of ultraviolet exposure, and after mixing and filling, the support structure is attached to a leader 47 at an interface 69. Coating with MAPTMS inside the support structure is typically done, as with the first described preferred embodiment, to promote wall adhesion. The filled support structure is placed in a shroud 71 to prevent exposure to ultraviolet, which would initiate polymerization and crosslinking. Leader 67 passes between a driven propulsion roller 73 and an idler roller 75. Roller 73 is driven by an electric motor 77 through a belt 79. An ultraviolet exposure zone 81 comprises ultraviolet lamps driven by a power supply 83. In operation the lamps are turned on, the motor is started, and the liquid filled tube is drawn through the exposure zone at a controlled velocity. Gelling occurs at a moving front relative to the length of the slab gel structure, substantially at the exposure zone, and still-liquid material in the slab gel structure that hasn't passed through the gelling zone flows in the support structure to replace the volume lost due to shrinkage.

A substantial difference in the heat initiated and the photoinitiated processes is in the initiation and the chemicals added to the mixtures to provide heat sensitivity or photosensitivity. The same flow and pressure relationships limiting the pulling rate hold in either case. There is a significant advantage in the photoinitiated case, in that the unexposed mixture does not gel in the dark, unlike the refrigerated mixture, in which the gelling rate is depressed. This provides a long shelf life for the liquid mixture prior to exposure, which is an advantage for commercial production. In addition, photoinitiation provides a sharp "on/off" switch for the gellation process, unlike thermal activation which is harder to control.

The limitations relative to capillary cross-section and support structure length that severely limit the useful and effective pulling rate are a clear disadvantage for commercial production purposes. These limitations may be overcome significantly by providing an elevated pressure at the end of the liquid-filled support structure that is the last to pass through the gelling zone, rather than relying on atmospheric pressure. This increases the pressure differential and allows a higher pulling rate to be employed than would otherwise be effective without incurring cavitation at the gel/solution interface. Typically, the pressure should be high enough at the start of the process that the pressure at the gel/solution interface is about $1.0 \times 10^6$ dynes/cm$^2$ (1 atmosphere). The elevated pressure may be supplied using standard techniques. In case of pressurization, the opposite end of the liquid-filled support structure is stoppered (closed) to prevent the pressure from forcing the liquid out that end before polymerization and wall adhesion commence. Such a pressure assist is especially important for long support structures.

It will be apparent to those skilled in the art that there are a large number of changes that may be made without departing substantially from the spirit and scope of the invention. For example, a very broad variety of chemical mixtures may be used to provide a liquid that can be induced to gel at a moving front by the application of energy at that front. The structure and detail of apparatus in the invention may vary as well. For example, the grooves may have different shapes, widths, depths, and separations, depending on their location on the plate. Also, more than one concentration of the first gelling liquid may be used in the grooves, i.e. the concentration could be changed from groove to groove. Similarly, the composition of the materials in the gelling liquid in the grooves could vary from groove to groove provided the materials used in each groove were compatible with the gelling material to be injected between the plates. Also, there are many ways to construct a useful cold chamber or dark chamber, and there are many ways of adding energy to initiate and influence gellation. Heat can be provided by such things as lasers, electron beams, other particle beams, electrical resistance, and high intensity infrared lights are examples. Also, ionizing radiation could be used directly, since it can be used to create cations in the mixture that can dissociate to form free radicals. Also, energy may be added by ion beams, and by other frequencies of electromagnetic radiation, such as microwaves, and in other ways, for example the ambient room temperature may be adequate for activation. Pulling devices for the gel support structures may be built in a wide variety of ways. All of these variations and others that will be apparent to those skilled in the art are considered within the scope and spirit of the invention as outlined in the appended claims.

I claim:

1. A method of casting a gradient slab gel comprising the steps of:
   filling a countable number of grooves in a first plate with a first gelling liquid;
   forming a gel casting region for a slab gel by spacing said first plate apart from a second plate so as to provide a flow path between said first and second plates which has a directional component orthogonal to said grooves;
   injecting a second gelling liquid into the gel casting region between said plates, such that said first liquid mixes with said second liquid as said second liquid encounters each said groove, forming a gelling mixture with a composition gradient;
   causing said gelling mixture in the gel casting region to gel, thereby forming a gradient slab gel.

2. The method of claim 1 wherein said spacing of said plates is performed after the filling of said grooves with said first gelling liquid.

3. The method claim 1 wherein the step of injecting is accomplished by capillary action.

4. The method of claim 1 wherein the step of causing the gelling mixture to gel comprises activating said gelling mixture sequentially from a first location to a second location in said gel casting region.

5. The method of claim 4 wherein said step of activating is accomplished by causing relative motion between an activating element and said support structure such that said activating element is moved along oone of said plates from a position next to said one of said plates opposite said first location to a position next to said one of said plates opposite said second location.

6. The method of claim 5 wherein said activating element comprises a source of energy and wherein said gelling mixture is activated by absorption of energy.

7. The method of claim 6 wherein said source of energy comprises a heater.

8. The method of claim 6 wherein said source of energy comprises a source of radiation.

9. The method of claim 8 wherein said radiation comprises ultraviolet light.

10. The method of claim 8 wherein said radiation comprises an electromagnetic radiation.

11. Apparatus for casting a gel comprising:
   a support structure for containing a gelling mixture that is promoted to gel by absorption of energy comprising:
   two substantially parallel plates that are spaced apart, at least one of said plates, hereinafter the first plate, constructed of a material that transmits energy;
   one or more substantially parallel edge seals positioned so as to define a liquid flow path between said plates; and
   a countable number of grooves situated on the surface of at least one of said plates wherein the grooves face the flow path;
   energy source means for providing energy at a localized area on said first plate;
   translation means for causing relative motion of said support structure and said energy source so that said localized area that receives energy from said source is moved along said first plate in a direction from the first end toward the second end of said first plate, thereby causing gelation to occur in said gelling mixture in a moving zone substantially adjacent to said localized area as said localized area moves.

12. Apparatus as in claim 11 wherein said energy source means comprises a heater.

13. Apparatus as in claim 12 further comprising refrigeration means for refrigerating those portions of said support structure containing said gelling mixture which, during the motion of said localized area, have not yet received energy from said energy source means, said refrigeration means for retarding gellation of said mixture in those said portions until they have been exposed to said heater.

14. Apparatus as in claim 12 wherein said heater comprises a radiation unit heated by electrical resistance.

15. Apparatus as in claim 12 wherein said heater comprises a lamp designed to radiate heat.

16. Apparatus as in claim 12 wherein said heat source comprises a circulating fluid that is thermostatically controlled.

17. Apparatus as in claim 16 wherein said circulating fluid is heated by an electrical resistance heater.

18. Apparatus as in claim 11 wherein said energy source means radiates electromagnetic energy in the range of wavelengths characterized as ultraviolet light.

19. Apparatus as in claim 18 further comprising shielding means for shielding from said ultraviolet light those portions of said support structure containing said mixture located between said moving zone and said second end of said plate.

20. A gel support structure for casting a gradient slab gel comprising:
   two substantially parallel plates that are spaced apart;
   one or more substantially parallel edge seals positioned so as to define a liquid flow path between said plates; and
   a countable number of grooves sitated on the surface of at least one of said plates wherein the grooves face the flow path, wherein said grooves are substantially linear and wherein said grooves are situated orthogonal to said edge seals.

21. A slab gel comprising:
   a) a support structure comprising:
      two substantially parallel plates that are spaced apart by 1000 microns or less; and
      a countable number of grooves situated on the surface of at least one of said plates wherein the grooves situated on the surface at least one of said plates wherein the grooves face the flow path; and
   b) a gel disposed in the flow path and grooves, said gel having a composition that forms a concentration gradient from one end of the flow path to the other end.

22. A slab gel a defined in claim 21 wherein said grooves are subsantially linear and wherein said grooves are situated orthogonal to said edge seals.

* * * * *